(12) United States Patent
Hedvati et al.

(10) Patent No.: US 7,763,749 B2
(45) Date of Patent: Jul. 27, 2010

(54) METHOD FOR THE PREPARATION OF PREGABALIN AND SALTS THEREOF

(75) Inventors: Lilach Hedvati, Doar Na Hefer (IL); Ziv Dee Noor, Haifa (IL); Claude Singer, Kfar Saba (IL); Gideon Pilarski, Holon (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 11/432,721

(22) Filed: May 10, 2006

(65) Prior Publication Data

US 2007/0073085 A1 Mar. 29, 2007

Related U.S. Application Data

(60) Provisional application No. 60/679,784, filed on May 10, 2005, provisional application No. 60/689,699, filed on Jun. 9, 2005.

(51) Int. Cl.
C07C 205/00 (2006.01)
(52) U.S. Cl. .................................... 562/553
(58) Field of Classification Search ................. 562/553
See application file for complete search history.

(56) References Cited

U.S. PATENT DOCUMENTS

| | | | |
|---|---|---|---|
| 5,010,189 A | 4/1991 | Herold et al. | |
| 5,599,973 A | 2/1997 | Silverman et al. | |
| 5,616,793 A | 4/1997 | Huckabee et al. | |
| 5,629,447 A * | 5/1997 | Huckabee et al. | 562/553 |
| 5,637,737 A | 6/1997 | Andres et al. | |
| 5,637,767 A | 6/1997 | Grote et al. | |
| 6,001,876 A | 12/1999 | Singh | |
| 6,187,930 B1 | 2/2001 | Torrens-Jover et al. | |
| 6,197,819 B1 | 3/2001 | Silverman et al. | |
| 6,333,198 B1 | 12/2001 | Edmeades et al. | |
| 6,488,964 B2 | 12/2002 | Bruna et al. | |
| 6,580,003 B2 | 6/2003 | Deng et al. | |
| 6,642,398 B2 | 11/2003 | Belliotti et al. | |
| 6,891,059 B2 | 5/2005 | Burk et al. | |
| 6,924,377 B2 | 8/2005 | Blazecka et al. | |
| 7,141,695 B2 | 11/2006 | Przewosny et al. | |
| 2001/0016665 A1* | 8/2001 | Grote et al. | 558/441 |
| 2003/0212290 A1 | 11/2003 | Burk et al. | |
| 2003/0225149 A1 | 12/2003 | Blazecka et al. | |
| 2005/0222464 A1 | 10/2005 | Hoge, II | |
| 2005/0228190 A1 | 10/2005 | Bao et al. | |
| 2005/0283023 A1 | 12/2005 | Hu et al. | |
| 2006/0270871 A1 | 11/2006 | Khanduri et al. | |
| 2007/0073085 A1 | 3/2007 | Hedvati et al. | |
| 2007/0191636 A1 | 8/2007 | Kansal et al. | |
| 2007/0197827 A1 | 8/2007 | Kansal et al. | |
| 2008/0014280 A1 | 1/2008 | Kumar et al. | |
| 2008/0311635 A1 | 12/2008 | Riva et al. | |

FOREIGN PATENT DOCUMENTS

| | | |
|---|---|---|
| CN | 1 634 869 | 7/2005 |
| CZ | 297 970 | 3/2007 |
| WO | WO 96/38405 A1 | 12/1996 |
| WO | WO 96/40617 A1 | 12/1996 |
| WO | WO 01/55090 A1 | 8/2001 |
| WO | WO 2005/100580 | 10/2005 |
| WO | WO 2006/000904 A2 | 1/2006 |
| WO | WO 2006/008640 | 1/2006 |
| WO | WO 2006/110783 | 10/2006 |
| WO | WO 2006/122255 | 11/2006 |
| WO | WO 2006/122258 | 11/2006 |
| WO | WO 2006/136087 | 12/2006 |
| WO | WO 2007/035789 | 3/2007 |
| WO | WO 2007/035890 | 3/2007 |
| WO | WO 2008/004044 | 1/2008 |
| WO | WO 2008/007145 | 1/2008 |
| WO | WO 2008/009897 | 1/2008 |
| WO | WO 2008/062460 | 5/2008 |
| WO | WO 2009/010554 | 1/2009 |

OTHER PUBLICATIONS

W.L.F. Armarego, D.D. Perrin, Purification of Laboratory Chemicals, 4th Editon 2002, Butterworth-Heinemann, p. 51.*

Martin et al. "Pregabalin: CI-1008, PD-144723" *Drugs of the Future*, vol. 24, No. 8, pp. 862-870, (1999).

Andruszkiewicz and Silverman, "A Convenient Synthesis of 3-Alkyl-4-Aminobutanoic Acids," *Synthesis*, 953-955 (1989).

Barnes, D.M., et al., "Development of a Catalytic Enantioselective Conjugate Addition of 1,3-Dicarbonyl Compounds to Nitroalkenes for the Synthesis of Endothelin-A Antagonist ABT-546. Scope, Mechanism, and Further Application to the Synthesis of the Antidepressant Rolipram," *J. Am. Chem. Soc.*, 124(44): 13097-13105 (2002).

Berner et al. "Asymmetric Michael Additions to Nitroalkenes," *European Journal of Organic Chemistry*, 1877-1894 (2002).

(Continued)

*Primary Examiner*—Daniel M Sullivan
*Assistant Examiner*—Sudhakar Katakam
(74) *Attorney, Agent, or Firm*—Kenyon & Kenyon LLP

(57) ABSTRACT

Processes for preparing and purifying Pregabalin and salts thereof are provided.

34 Claims, No Drawings

OTHER PUBLICATIONS

Cason, J. et al., "Branched-Chain Fatty Acids. XXVII. Further Study of the Dependence of Rate of Amide Hydrolysis on Substitution near the Amide Group. Relative Rates of Hydrolysis of Nitrile to Amide and Amide to Acid," *J. Org. Chem.*, 18(9): 1129-1136 (1953).

Chen, AO et al., "Synthesis of Pregabalin," *Zhongguo YiYao Gongye Zazhi*, 35(4): 195-196 (2004).

Colonge et al., "Preparation De Pyrrolidones-2 et de Gamma-Aminoacides," *Bulletin De La Societe Chimique De France, Societe Francaise De Chimie*, 598-603 (1962).

Day and Thorpe, "The Formation and Reactions of Imino-compounds. Part XX. The Condensation of Aldehydes with Cyanoacetamide," *J. Chem. Soc.*, 117: 1465-1474 (1920).

Hoekstra, M.S. et al., "Chemical Development of C1-1008, an Enantiomerically Pure Anticonvulsant," *Organic Process Research and Development*, 1(1): 26-38 (1997).

Karanewsky, D.S. et al., "Practical Synthesis of an Enantiomerically Pure Synthon for the Preparation of Mevinic Acid Analogues," *J. Org. Chem.*, 56(11): 3744-3747 (1991).

Li, H. et al., "Highly Enantioselective Catalytic Conjugate Addition of Malonate and β- Ketoester to Nitroalkenes: Asymmetric C-C Bond Formation with New Bifunctional Organic Catalysts Based on Cinchona Alkaloids," *J. Am. Chem. Soc.*, 126(32): 9906-9907 (2004).

Okino, T. et al., "Enantio- and Diastereoselective Michael Reaction of 1,3-Dicarbonyl Compounds to Nitroolefins Catalyzed by a Bifunctional Thiourea," *J. Am. Chem. Soc.*, 127(1): 119-125 (2005).

Sammis, G.M. et al., "Highly Enantioselective Catalytic Conjugate Addition of Cyanide to α,β-Unsaturated Imides", *J. Am. Chem. Soc.*, 125(15): 4442-43 (2003).

Shintani, Ryo et al., "Highly Enantioselective Desymmetrization of Anhydrides by Carbon Nucleophiles: Reactions of Grignard Reagents in the Presence of (−)-Sparteine," *Angewandte Chemie, International Edition*, 41(6): 1057-1059 (2002).

Snyder et al., Introduction to Modern Liquid Chromatography, 549-572 (2d ed., John Wiley & Sons, 1979).

Strobel et al., Chemical Instrumentation: A Systematic Approach, 391-393, 879-894, 922-925, 953 (3d ed. 1989).

Theisen, P.D. et al., "Prochiral Recognition in the Reaction of 3-Substituted Glutaric Anhydrides with Chiral Secondary Alcohols," *J. Org. Chem.*, 58(1): 142-146 (1993).

Verma, Rekha et al., "Desymmetrization of prochiral anhydrides with Evans' oxazolidinones: an efficient route to homochiral glutaric and adipic acid derivatives," *J. Chem. Soc., Perkin Transactions I: Organic and Bio-Organic Chemistry*, 257-264 (1999).

Yamamoto et al., "Stereoselective Synthesis of (E)-Alkylidenesuccinates by Palladium-catalyzed Carbonylation," *Bull. Chem. Soc. Japan*, 58(11): 3397-3398 (1985).

Burk et al., "An Enantioselective Synthesis of (S)-(+)-3-Aminomethyl-5-methylhexanoic Acid via Asymmetric Hydrogenation," *J. Org. Chem.*, 68: 5731-5734 (2003).

Lin et al., "Chiral HPLC Separations for Process Development of S-(+)-Isobutyl GABA, A Potential Anti-Epileptic Agent," *J. Liq. Chrom.*, 19(16):2699-2708 (1996).

Serfass et al., "General Synthesis of 3-Substituted Alkenyl GABA as Potential Anticonvulsants," *Biorganic & Medicinal Chemistry Letters*, 8: 2599-2602 (1998).

Yuen et al., "Enantioselective Synthesis of PD144723: A Potent Stereospecific Anticonvulsant," *Biorganic & Medicinal Chemistry Letters*, 4(6): 823-826 (1994).

* cited by examiner

METHOD FOR THE PREPARATION OF PREGABALIN AND SALTS THEREOF

RELATED APPLICATIONS

This application claims the benefit of U.S. Provisional Application Nos. 60/679,784, filed May 10, 2005, and 60/689,699, filed Jun. 9, 2005, the contents of which are incorporated herein in their entirety by reference.

FIELD OF THE INVENTION

The present invention is directed to processes for preparing and purifying Pregabalin and salts thereof.

BACKGROUND OF THE INVENTION (S)-Pregabalin, 3-(aminomethyl)-5-methyl-(3S)-hexanoic acid, which is also known as (S)-(+)-3-(aminomethyl)-5-methylhexanoic acid, has the empirical formula $C_8H_{17}NO_2$ and a molecular weight of 159, and may be represented by the chemical structure:

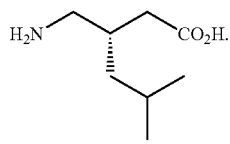

(S)-Pregabalin has been developed as a follow-up compound to Gabapentin, NEURONTIN®, for use in the treatment of epilepsy, pain, anxiety, and social phobia. Both (S)-Pregabalin and gabapentin are analogs of 4-aminobutyric acid (GABA), a neurotransmitter that is thought to play a major inhibitory role in the central nervous system (CNS). (S)-Pregabalin (PRG) has been approved in US for the treatment of nerve pain associated with diabetes and shingles, as of Dec. 31, 2004. (S)-Pregabalin is available as LYRICA™ in tablets for 25, 50, 75, 150, 200, and 300 mg doses.

(S)-Pregabalin, which is also known as γ-amino butyric acid or (S)-3-isobutyl GABA, has been found to activate GAD (L-glutamic acid decarboxylase), has a dose dependent protective effect on-seizure, and is a CNS-active compound. (S)-Pregabalin has been found to be useful in anticonvulsant therapy, due to its activation of GAD, promoting the production of GABA, one of the brain's major inhibitory neurotransmitters, which is released at 30 percent of the brains synapses. (S)-Pregabalin has analgesic, anticonvulsant, and anxiolytic activity.

The preparation of (S)-Pregabalin described in DRUGS OF THE FUTURE, 24 (8), 862-870 (1999) is done according to the following scheme:

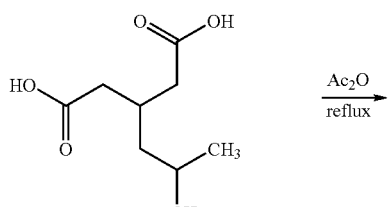

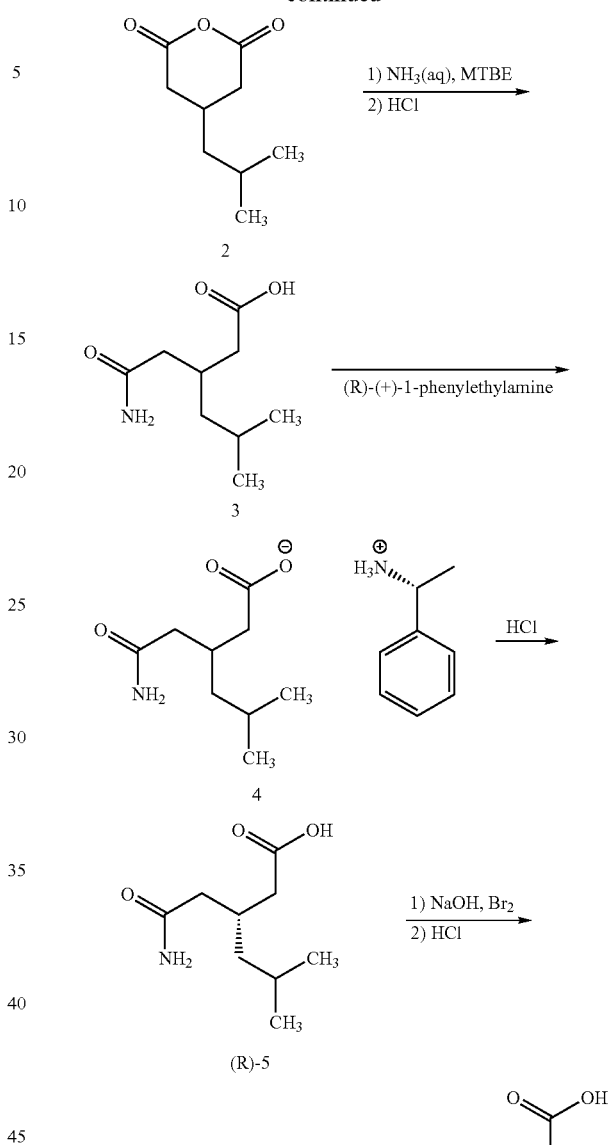

wherein, (R)-(−)-3-(carbamoylmethyl)-5-methylhexanoic acid of formula 5, a key intermediate in the synthesis, is converted to (S)-Pregabalin via a Hoffmann degradation with $Br_2$/NaOH, followed by precipitation of (S)-Pregabalin, after addition of HCl.

A very similar process is disclosed in U.S. Pat. No. 5,616,793, wherein (S)-Pregabalin is also obtained by the Hoffman degradation, followed by precipitation of (S)-Pregabalin, after addition of HCl. The product is further purified by crystallization from a mixture of isopropanol and water.

Hence, there is a need in the art for a process for the preparation and purification of Pregabalin and salts thereof.

SUMMARY OF THE INVENTION

In one embodiment, the present invention provides a process for the preparation of Pregabalin comprising combining an alkali hydroxide and water; adding 3-(carbamoylmethyl)-5-methylhexanoic acid (referred to as CMH) at a temperature of about 0° C. to about 40° C.; adding bromine, in a drop-wise manner, at a temperature of about 0° C. to about 40° C.; heating; reacting with a strong mineral acid; extracting with a $C_{4-8}$ alcohol, and mixing with a base.

In a further embodiment, the present invention provides a process for the preparation of Pregabalin comprising combining water and an alkali hydroxide selected from a group consisting of sodium hydroxide, potassium hydroxide, lithium hydroxide and cesium hydroxide; adding CMH at a temperature of about 5° C. to about 10° C.; adding bromine, in a drop-wise manner, at a temperature of about 5° C. to about 10° C.; heating to a temperature of about 40° C. to about 100° C.; reacting with a strong mineral acid selected from a group consisting of $H_2SO_4$, HCl, HBr and $H_3PO_4$; heating to a temperature of about 30° C. to about 40° C., and mixing with a base selected from a group consisting of diisopropylaamine, dipropylamine, tributyl amine, triethyl amine, sodium hydroxide, potassium hydroxide, cesium hydroxide, sodium carbonate, sodium bicarbonate and potassium carbonate.

In one embodiment, the present invention provides a process for the preparation of the alkali salt of Pregabalin comprising combining an alkali hydroxide and water; adding CMH at a temperature of about 0° C. to about 40° C.; adding bromine, in a drop-wise manner, at a temperature of about 0° C. to about 40° C., and heating; wherein the alkali salt of Pregabalin is, preferably, Pregabalin sodium.

In a further embodiment, the present invention provides a process for the preparation of Pregabalin by preparing the alkali salt of Pregabalin, and converting it to Pregabalin.

DETAILED DESCRIPTION OF THE INVENTION

As used herein, unless specified otherwise, the term "CMH" refers to either the R enantiomer of CMH ((R)-CMH) or to the CMH racemate.

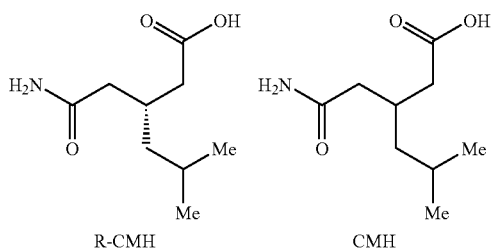

R-CMH              CMH

As used herein, unless specified otherwise, the term "Pregabalin" refers to either the S enantiomer of Pregabalin ((S)-Pregabalin) or to the Pregabalin racemate.

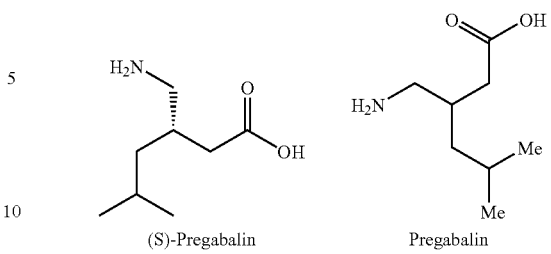

(S)-Pregabalin              Pregabalin

As used herein, unless specified otherwise, when CMH racemate is used, Pregabalin racemate is obtained.

As used herein, unless specified otherwise, when (R)-CMH is used, (S)-Pregabalin is obtained.

As used herein, unless specified otherwise, the term "Pregabalin alkali salt" refers to either the S enantiomer of Pregabalin alkali salt or to the racemate Pregabalin alkali salt,

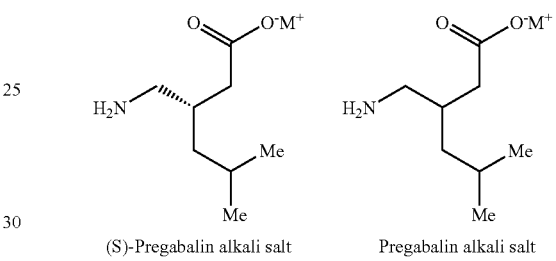

(S)-Pregabalin alkali salt              Pregabalin alkali salt wherein M is an alkali metal.

The present invention relates to a process for preparing Pregabalin, wherein it is obtained in high yields and purity. The process comprises maintaining at low temperatures the aqueous solution of the alkali hydroxide when combining with CMH, and when adding bromine, in a drop-wise manner. Hence, controlling the temperature during the additions, allows controlling the amount of impurities formed during the reaction. The process also includes purifying Pregabalin by preparation of its acidic salt, without isolating it, followed by selective extractions of the acidic salt of Pregabalin by the utilization of carefully chosen solvents and/or mixtures of solvents. Since a highly pure form, typically greater than 99.5 percent, of any drug is generally required for human treatment, a method that combines the control of the formation of impurities and a facile final purification is particularly advantageous.

The present invention provides a process for the preparation of Pregabalin comprising combining an alkali hydroxide and water; adding CMH at a temperature of about 0° C. to about 40° C.; adding bromine, in a drop-wise manner, at a temperature of about 0° C. to about 40° C.; heating; reacting with a strong mineral acid; extracting with a $C_{4-8}$ alcohol, and mixing with a base.

Preferably, the preparation of Pregabalin may be done by combining water and an alkali hydroxide is selected from a group consisting of sodium hydroxide, potassium hydroxide, lithium hydroxide and cesium hydroxide; adding CMH at a temperature of about 5° C. to about 10° C.; adding bromine, in a drop-wise manner, at a temperature of about 5° C. to about 10° C.; heating to a temperature of about 40° C. to about 100° C.; reacting with a strong mineral acid selected from a group consisting of $H_2SO_4$, HCl, HBr and $H_3PO_4$; heating to a temperature of about 30° C. to about 40° C., extracting with a $C_{4-8}$ alcohol selected from a group consisting of butanol, iso-butanol, 2-butanol, pentanol and iso-pentanol, and mixing with a base selected from a group consisting of diisopropylamine, dipropylamine, tributyl amine, triethyl amine, sodium hydroxide, potassium hydroxide, cesium hydroxide, sodium carbonate, sodium bicarbonate and potassium carbonate.

The present invention further provides a process for the preparation of Pregabalin comprising combining water and an alkali hydroxide selected from a group consisting of sodium hydroxide, potassium hydroxide, lithium hydroxide and cesium hydroxide; adding CMH at a temperature of about 5° C. to about 10° C.; adding bromine, in a drop-wise manner, at a temperature of about 5° C. to about 10° C.; heating to a temperature of about 40° C. to about 100° C.; reacting with a strong mineral acid selected from a group consisting of $H_2SO_4$, HCl, HBr and $H_3PO_4$; heating to a temperature of about 30° C. to about 40° C., and mixing with a base selected from a group consisting of diisopropylamine, dipropylamine, tributyl amine, triethyl amine, sodium hydroxide, potassium hydroxide, cesium hydroxide, sodium carbonate, sodium bicarbonate and potassium carbonate.

The present invention also provides a process for the preparation of the alkali salt of Pregabalin comprising combining an alkali hydroxide and water; adding CMH at a temperature of about 0° C. to about 40° C.; adding bromine, in a drop-wise manner, at a temperature of about 0° C. to about 40° C., and heating; wherein the alkali salt of Pregabalin is, preferably, Pregabalin-sodium.

The present invention also provides a process for the preparation of Pregabalin by preparing the alkali salt of Pregabalin, and converting it to Pregabalin.

Preferably, the alkali metal is selected from a group consisting of sodium, potassium, lithium, and cesium. More preferably, the alkali metal is sodium.

Preferably, the alkali hydroxide is sodium hydroxide. Preferably, an aqueous solution of the alkali hydroxide is used. Typically, the aqueous solution of the alkali hydroxide is concentrated. Preferably, the concentration is of about 5 to about 20 molar, more preferably of about 5 to about 10 molar. Typically, such solutions have a pH of at least about 13, preferably at least about 14.

Preferably, bromine is added in an amount of 1 mole equivalents to about 1.4 mole equivalents per mole equivalents of CMH. Preferably, the drop-wise addition is done over a period of about 12 minutes to about 180 minutes, more preferably, of about 30 to about 45 minutes.

Preferably, heating, after the addition of bromine, is done to a temperature of about 60° C. to about 85° C.

Preferably, heating, after the addition of bromine, is done for about 15 minutes to about 4 hours, more preferably, for about 15 minutes to about an hour, prior to the addition of the strong mineral acid.

Preferably, cooling to a temperature of about 40° C. to about 20° C. is done, prior to the addition of the strong mineral acid.

Preferably, the strong mineral acid is $H_2SO_4$. Preferably, when adding the strong mineral acid, a salt of Pregabalin with the strong mineral acid may be obtained. Preferably, after adding the acid, heating to a temperature of about 30° C. to about 35° C. is done. Preferably, a pH of less than about 3 is obtained when the strong mineral acid is added.

Preferably, the salt may be purified without isolating it. This salt is purified by selective extractions with $C_{4-8}$ alcohol. The extractions are selective due to the difference in the solubility of the salt in water vs. the solubility of the impurities in water. Preferably, the extractions with $C_{4-8}$ alcohol are done, prior to the addition of the base. The preferred $C_{4-8}$ alcohol is iso-butanol.

Preferably, the organic phase obtained from the extraction process is cooled to a temperature of about 10° C. to about 0° C., more preferably, to about 2° C., followed by filtering off the inorganic salts obtained in the reaction. Preferably, the filtrate is combined with a base, to obtain a precipitate of Pregabalin. Optionally, the organic phase may be combined with the base without filtering the inorganic salts. Preferably, the base is either an organic base or an inorganic base. The preferred organic base is either a secondary or tertiary amine. Preferably, the secondary amine is either diisopropylamine or dipropylamine. More preferably, the secondary amine is diisopropylamine. A preferred tertiary amine is either tributyl amine or triethyl amine. More preferably, tertiary amine is tributyl amine. Preferably, the inorganic base is either an alkali hydroxide or an alkali carbonate. A preferred alkali hydroxide is sodium hydroxide, potassium hydroxide, lithium hydroxide, or cesium hydroxide. More preferably, the alkali hydroxide is sodium hydroxide. A preferred alkali carbonate is sodium carbonate, sodium bicarbonate, or potassium carbonate. More preferably, the alkali carbonate is sodium carbonate. The more preferred inorganic base is alkali carbonate, most preferably, sodium carbonate. The more preferred base is an organic base, most preferably, a tertiary amine, and even most preferably, tributylamine.

When Pregabalin alkali salt is prepared, the heating step, after the addition of bromine, further comprises stirring at a temperature of about 40° C. to about 80° C., more preferably, at about 50° C. Preferably, after stirring at about 50° C., cooling to a temperature of about 10° C. to about 0° C., more preferably, to about 0° C. is done, to obtain a precipitate of the salt, which is then recovered. Pregabalin alkali salt may be recovered by filtration, washing, preferably, with water, and drying under vacuum, preferably at a temperature of about 45° C.

Preferably, the conversion of the alkali salt of Pregabalin to Pregabalin may be done by mixing the salt; adding a strong mineral acid, and adding a base.

Preferably, mixing the alkali salt with a strong mineral acid provides the acidic salt of Pregabalin, which is purified by extractions, as described before. After that, to the organic phase is added a base, providing Pregabalin, also, as described before.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

EXAMPLES

Example 1

Preparation of Pregabalin-Sodium (PRG-Na)

A 0.5 liter reactor was loaded with 160 ml of water and 58 g of NaOH. The solution was cooled to from about 10° to about 15° C., and 40 g of CMH were added. The mixture was stirred, and 40 g of $Br_2$ were added drop-wise over a period of 45 minutes, while maintaining the temperature at less than 20° C. The mixture was heated to 85° C. for 15 minutes, stirred at 50° C. for an hour, and cooled to 0° C. The Pregabalin-Na was filtered, washed with 40 ml of water, and dried at 45° C. under vacuum, producing a 90 percent yield.

Example 2

Preparation of Pregabalin from Pregabalin-Sodium

A 0.1 liter reactor was loaded with 12 ml of water and 7.5 g of Pregabalin-Na. The mixture was stirred, and a 32 percent aqueous solution of HCl was added drop-wise to lower the pH to 0. The solution was then extracted with 25 ml of iso-butanol, the organic layer was separated, and tributyl amine, $Bu_3N$, was added in an amount sufficient to provide a pH of 4.6. The mixture was then cooled to 0° C., and the resulting Pregabalin precipitate was filtered and dried at 55° C. under vacuum, providing a 54 percent yield. Purity 98.6%

Example 3

Preparation of Pregabalin from Pregabalin-Sodium

A 0.1 liter reactor was loaded with 12 ml of water and 7.5 g of Pregabalin-Na. The mixture was stirred, and an aqueous 32 percent HCl solution was added drop-wise in an amount sufficient to lower the pH to 0. The solution was extracted with 25 ml of pentanol, the organic layer was separated, and $Bu_3N$ was added in an amount sufficient to provide a pH of 4.6. The mixture was then cooled to 0° C., and the Pregabalin precipitate was filtered and dried at 55° C. under vacuum, providing a 72 percent yield. Purity 98%

Example 4

Preparation of Pregabalin

A 0.2 liter reactor was loaded with 60 ml of water and 17.65 g of NaOH. The solution was cooled to from 10° to 15° C., and 15 g of CMH were added. Then, 15 g of $Br_2$ were added drop-wise over a period of 15 minutes, while maintaining the temperature at less than 20° C. The mixture was heated to 80° C. for 15 minutes, and then cooled to room temperature, i.e., about 20° to about 25° C. An aqueous 32 percent solution of HCl was added in an amount sufficient to provide a pH of 1. The solution was then divided to two portions.

Portion I was extracted with 37 ml of iso-butanol, the organic layer was separated, and $Bu_3N$ was added in an amount sufficient to provide a pH of 4. The Pregabalin was precipitated, filtered, and washed with 10 ml of iso-butanol. After drying at 55° C. under vacuum, Pregabalin was obtained as white crystals in a 71 percent yield. Purity 97.2%

Portion II was extracted with 37 ml of pentanol, the organic layer was separated, and $Bu_3N$ was added in an amount sufficient to provide a pH of 4. The Pregabalin was precipitated, filtered, and washed with 10 ml of pentanol. After drying at 55° C. under vacuum, Pregabalin was obtained as white crystals in a 73 percent yield. Purity 93.1%

Example 5

Preparation of Pregabalin

A 0.1 liter reactor was loaded with 60 ml of water and 17.6 g of NaOH. The solution was cooled to from 10° to 15° C., and 15 g of CMH were added. The mixture was stirred, and 15 g of $Br_2$ were added drop-wise over a period of 45 minutes, while maintaining the temperature at less than 20° C. The mixture was heated to 85° C. for 15 minutes, and then was cooled to about 20 to about 25° C. Then, 12.4 ml of $H_2SO_4$ were added drop-wise in an amount sufficient to lower the pH to 1, and the resulting solution was divided to two portions.

Portion I was extracted with 37 ml of iso-butanol. The organic layer was separated, and $Bu_3N$ was added in an amount sufficient to provide a pH of 4, precipitation of Pregabalin, which was filtered, and washed with 10 ml of iso-butanol. After drying at 55° C. under vacuum, Pregabalin was obtained as white crystals in a 63 percent yield. Purity 99.1%

Portion II was extracted with 37 ml of pentanol, the organic layer was separated, and $Bu_3N$ was added in an amount sufficient to provide a pH of 4. The precipitated Pregabalin was filtered, and washed with 10 ml of pentanol. After drying at 55° C. under vacuum, Pregabalin was obtained as white crystals in a 61 percent yield. Purity 96.6%

Example 6

Preparation of Pregabalin

A 0.2 liter reactor was loaded with 60 ml of water and 17.65 g of NaOH. The resulting solution was cooled to from 10° to 15° C., and 15 g of CMH were added. Then, 15 g of $Br_2$ were added drop-wise over 15 minutes, while maintaining the temperature at less than 20° C. The mixture was heated to 80° C. for 15 minutes, and then cooled to room temperature, i.e., about 20 to about 25° C. Then, 75 ml of iso-butanol were added, and an aqueous 32 percent solution of HCl was added in an amount sufficient to provide a pH of 2. The organic phase was separated, and Pregabalin was precipitated after the addition of 14 ml of $Bu_3N$. The mixture was cooled to 2° C., and the solid was filtered, washed, and dried at 55° C. under vacuum, providing a 61 percent yield. Purity 98.7%

Example 7

Preparation of Pregabalin

A 0.2 liter reactor was loaded with 60 ml of water and 17.65 g of NaOH. The solution was cooled to from 10° to 15° C., and 15 g of CMH were added. Then, 15 g of $Br_2$ were added drop-wise over 15 minutes, while maintaining the temperature at less than 20° C. The mixture was heated to 80° C. for 15 minutes, and then cooled to room temperature, i.e., about 20 to about 25° C. Then 75 ml of pentanol were added, followed by an aqueous 32 percent HCl solution in an amount sufficient to provide a pH of 2. The organic phase was separated, and Pregabalin was precipitated after the addition of 14 ml of $Bu_3N$. The mixture was then cooled to 2° C., and the solid was filtered, washed, and dried at 55° C. under vacuum, providing a 52 percent yield. Purity 96.9%

Example 8

Preparation of Pregabalin

A 0.2 liter reactor was loaded with 110 ml of water and 27.65 g of NaOH. The solution was cooled to from 10° to 15° C., and 23.5 g of CMH were added. Then, 23.5 g of $Br_2$ were added drop-wise over 15 minutes, while maintaining the temperature at less than 20° C. The mixture was heated to 80° C. for 15 minutes, and then cooled to room temperature, i.e., about 20 to about 25° C. An aqueous 32 percent solution of HCl was added in an amount sufficient to provide a pH of 2. The mixture was then extracted with 138 ml of iso-butanol, and the organic phase was separated. Pregabalin precipitated after the addition of diisopropylethyl amine in an amount sufficient to provide a pH of 4. The mixture was cooled to 2° C., and the solid was filtered, washed, and dried at 55° C. under vacuum, providing a 43 percent yield. Purity 96.9%

Example 9

Preparation of Pregabalin

A reactor (1 L) was loaded with water (200 ml) and NaOH (34.7 g). The solution was cooled to 5° C. and CMH (40 g) was added. $Br_2$ (34.7 g) was added dropwise (15 min) while keeping the temperature below 10° C. The mixture was heated to 60° C. for 15 min and then cooled to RT. Iso-butanol (120 ml) and then a solution of $H_2SO_4$-66% (40 ml) were added (pH=3). The mixture was heated to 33° C., then the phases were separated, and the aqueous phase was extracted with Iso-butanol (100 ml). The combined organic phases was cooled to 2° C. for 2.5 h, and filtered to remove inorganic salts. The filtrate was heated to room temperature, and $Bu_3N$ (41.6 g) was added to the organic phase. The mixture was heated to dissolution and then was cooled to 2° C., and stirred for 2 h. The solid was filtered and the cake washed with i-BuOH (40 ml). A sample (3 g) was dried at 45° C. in a vacuum oven overnight. The weight loss was 32%. This implies a calculated yield of 79.4%. Purity 99.5%.

Example 10

Preparation of (S)-Pregabalin

A reactor (0.2 L) was loaded with water (150 ml) and NaOH (32.3 g) to obtain a solution. The solution was cooled to 5° C. and (R)-CMH (30 g) was added. $Br_2$ (25.9 g) was then added dropwise (15 min) while keeping the temperature below 10° C. The mixture was heated to 60° C. for 15 minutes and then cooled to RT. Iso-butanol was added (90 ml) and then a solution of $H_2SO_4$ (66%) (32 ml). The phases were separated, and the aqueous phase was extracted with Iso-butanol (75 ml). $Bu_3N$ (32.6 ml) was added to the combined organic phases. The mixture was heated to dissolution and then was cooled to 2° C., and stirred for 1.5 hours. The solid was filtered, washed, and dried at 55° C. under vacuum, providing an 80.4% yield. Total purity: 99.7% area by HPLC.

Example 11

Preparation of (S)-Pregabalin

A reactor (0.1 L) was loaded with water (50 ml) and NaOH (10.8 g) to obtain a solution. The solution was cooled to 15° C. and (R)-CMH (10 g) was added. $Br_2$ (8.6 g) was added dropwise (15 min) while keeping the temperature below 20° C. The mixture was heated to 60° C. for 15 min and then cooled to RT. Iso-butanol (60 ml) and then a solution of $H_2SO_4$ (66%) (10 ml) were added. The phases were separated, and the aqueous phase was extracted with Iso-butanol (25 ml). To the combined organic phases $Bu_3N$ (9.9 g) was added and the mixture was cooled to 2° C., and stirred for 2 hours. The solid was filtered, washed and dried at 55° C. under vacuum, providing (S)-PREGABALIN with total purity 99.88% area by HPLC.

Example 12

Preparation of (S)-Pregabalin

A reactor (0.5 L) was loaded with water (165 ml) and NaOH (35.5 g) to obtain a solution. The solution was cooled to 15° C. and (R)-CMH (33 g) was added. $Br_2$ (28.51 g) was added dropwise (15 min) while keeping the temperature below 25° C. The mixture was heated to 60° C. for 15 min and then cooled to 15° C. Iso-butanol was added (100 ml) and then a solution of $H_2SO_4$ (66%) (33 ml) was added. The phases were separated, and the aqueous phase was extracted with Iso-butanol (83 ml). To the combined organic phases $Bu_3N$ (34.2 g) was added and the mixture was cooled to 2° C., and stirred for 2 hours. The solid was filtered, washed and dried at 55° C. under vacuum, providing (S)-PREGABALIN with total purity 99.86% area by HPLC.

What is claimed is:

1. A process for the preparation of Pregabalin comprising:
    a) combining an alkali hydroxide and water;
    b) adding CMH at a temperature of about 0° C. to about 40° C.;
    c) adding bromine, in a drop-wise manner, at a temperature of about 0° C. to about 40° C., to form a mixture;
    d) heating the mixture formed in step c);
    e) reacting the heated mixture with a strong mineral acid to form an acid salt of pregabalin;
    f) extracting the acid salt of pregabalin with a $C_{4-8}$ alcohol; and
    g) mixing the extracted pregabalin acid salt with a base to obtain Pregabalin.

2. The process of claim 1, wherein the alkali hydroxide is selected from a group consisting of sodium hydroxide, potassium hydroxide, lithium hydroxide, and cesium hydroxide.

3. The process of claim 1, wherein CMH is added, in step b, at a temperature of about 5° C. to about 10° C.

4. The process of any of claim 1, wherein bromine is added, in step c, at a temperature of about 5° C. to about 10° C.

5. The process of claim 1, wherein bromine is added in an amount of 1 mole equivalents to about 1.4 mole equivalents per mole equivalents of CMH.

6. The process of claim 1, wherein the drop-wise addition, in step b, is done over a period of about 12 minutes to about 180 minutes.

7. The process of claim 1, wherein heating, in step d, is done to a temperature of about 40° C. to about 100° C.

8. The process of claim 1, wherein the heating, in step d, is done for about 15 minutes to about 4 hours.

9. The process of claim 1, wherein cooling to a temperature of about 40° C. to about 20° C. is done, prior to step e.

10. The process of claim 1, wherein the strong mineral acid selected from a group consisting of $H_2SO_4$, HCl, HBr, and $H_3PO_4$.

11. The process of claim 10, wherein the strong mineral acid is $H_2SO_4$.

12. The process of claim 1, wherein a pH of less than about 3 is obtained when the strong mineral acid is added.

13. The process of claim 1, further comprising heating, prior to the extraction in step f, to a temperature of about 30° C. to about 35° C.

14. The process of claim 1, further comprising cooling to a temperature of about 10° C. to about 0° C., and filtering off the inorganic salts, prior to the addition of the base.

15. The process of claim 1, wherein the base is an organic base.

16. The process of claim 15, wherein the organic base is either a secondary or tertiary amine.

17. The process of claim 16, wherein the secondary amine is either diisopropylamine or dipropylamine.

18. The process of claim 17, wherein the secondary amine is diisopropylamine.

19. The process of claim 16, wherein the tertiary amine is either tributyl amine or triethyl amine.

20. The process of claim 19, wherein the tertiary amine is tributyl amine.

21. The process of claim 1, wherein the base is an inorganic base.

22. The process of claim 21, wherein the inorganic base is either an alkali hydroxide or an alkali carbonate.

23. The process of claim 22, wherein the alkali hydroxide is sodium hydroxide, potassium hydroxide, lithium hydroxide, or cesium hydroxide.

24. The process of claim 23, wherein the alkali hydroxide is sodium hydroxide.

25. The process of claim 22, wherein the alkali carbonate is sodium carbonate, sodium bicarbonate, or potassium carbonate.

26. The process of claim 25, wherein the alkali carbonate is sodium carbonate.

27. The process of claim 1, wherein the base is tributylamine.

28. The process of claim 1, wherein CMH is R-CMH.

29. The process of claim 1, wherein Pregabalin is (S)-Pregabalin.

30. The process of claim 2, wherein the alkali hydroxide is sodium hydroxide.

31. The process of claim 30, wherein the alkali hydroxide is in a form of an aqueous solution.

32. The process of claim 7, wherein, heating in step d, is done to a temperature of about 60° C. to about 85° C.

33. The process of claim 1, wherein the $C_{4-8}$ alcohol is selected from a group consisting of butanol, iso-butanol, 2-butanol, pentanol, and iso-pentanol.

34. The process of claim 33, wherein the $C_{4-8}$ alcohol is iso-butanol.

* * * * *